(12) United States Patent
Ho et al.

(10) Patent No.: US 7,211,274 B2
(45) Date of Patent: May 1, 2007

(54) HAIR GROWTH FORMULATION

(75) Inventors: David Sue San Ho, Ipoh (MY); Kah Hay Yuen, Penang (MY); Jia Woei Wong, Ipoh (MY); Ai Beoy Lim, Pulau (MY)

(73) Assignee: Hovis SDN BHD (MY)

( * ) Notice: Subject to any disclaimer, the term of this patent is extended or adjusted under 35 U.S.C. 154(b) by 0 days.

(21) Appl. No.: 11/120,268

(22) Filed: May 2, 2005

(65) Prior Publication Data

US 2005/0191260 A1 Sep. 1, 2005

Related U.S. Application Data

(63) Continuation of application No. 10/440,564, filed on May 17, 2003, now abandoned.

(30) Foreign Application Priority Data

May 22, 2002 (MY) .......................... PI 2002 1894

(51) Int. Cl.
*A61K 9/48* (2006.01)
*A61K 9/64* (2006.01)

(52) U.S. Cl. ...................................... 424/451; 424/456

(58) Field of Classification Search ................ 424/456, 424/451; 514/456
See application file for complete search history.

(56) References Cited

U.S. PATENT DOCUMENTS

| 4,439,432 A | * | 3/1984 | Peat | 514/177 |
| 5,545,398 A | * | 8/1996 | Perricone | 424/59 |
| 5,591,772 A | * | 1/1997 | Lane et al. | 514/458 |
| 6,369,042 B1 | * | 4/2002 | Oberthur et al. | 514/54 |
| 2003/0182679 A1 | * | 9/2003 | Geiger et al. | 800/278 |

FOREIGN PATENT DOCUMENTS

JP 2000038340 * 2/2000

* cited by examiner

*Primary Examiner*—Alton Pryor
(74) *Attorney, Agent, or Firm*—David G. Oberdick, Esq.; Christian M. Best, Esq.; Meyer, Unkovic & Scott LLP

(57) ABSTRACT

The present invention relates to a formulation for promoting hair growth and preventing hair loss. Supplementation with the formulation promotes hair growth and increases the number of hairs in mammals. In one embodiment, a composition for promoting hair growth and reducing hair loss according to the present invention comprises mixed tocotrienols and a pharmaceutically acceptable excipient.

8 Claims, 1 Drawing Sheet

HAIR GROWTH FORMULATION

CROSS-REFERENCE TO RELATED APPLICATIONS

This patent claims priority from the patent applications of the same name, one of which was filed in Malaysia on May 22, 2002 and assigned Malaysian patent application number PI20021894, and the other which was filed in the United States on May 17, 2003 and assigned U.S. patent application Ser. No. 10/440,564. The present application is a continuation of application Ser. No. 10/440,564, filed May 17, 2003, now abandoned.

TECHNICAL FIELD OF THE INVENTION

The present invention generally relates to a hair growth formulation, in particular to a formulation comprising tocotrienol for promoting hair growth.

BACKGROUND OF THE INVENTION

Hair loss or alopecia is a common problem in both males and females regardless of their age. There are several types of hair loss, such as androgenetic alopecia, alopecia greata, telogen effluvium, hair loss due to systemic medical problems, e.g., thyroid disease, adverse drug effects and nutritional deficiency states as well as hair loss due to scalp or hair trauma, discoid lupus erythematosus, lichen planus and structural shaft abnormalities. (Hogan and Chamberlain, 2000). Of the above, androgenetic alopecia is the most common cause of hair loss, affecting about 30% of individuals who have a strong family history of hair loss. (Bergfeld, 1988). Androgenetic alopecia is caused by three interdependent factors: male hormone dihydrotestosterone (DHT), genetic disposition and advancing age. DHT causes hair follicles to degrade and further shrink in size, resulting in weak hairs. DHT also shortens the anagen phase of the hair follicle growing cycle. Over time, more hairs are shed and hairs become thinner. Possible options for the treatment of alopecia include reassurance, hair prosthesis, surgery and topical/oral medications. (Hogan & Chamberlain, 2000; Bertolino, 1993; Setty, 1970).

The most common pharmacological management of androgenetic alopecia is topical minoxidil and finasteride taken orally. The main problem with topical minoxidil therapy is patient compliance, although it has been shown to be effective in a few studies. (DeVillez et al, 1994; Trancik R J, 1998). On the other hand, oral finasteride is associated with significant adverse effects such as decreased libido, impotence and ejaculation disorders. (Chen et al, 1996).

In addition, there is a report by Goldman et al. (1996) which evaluates whether male pattern baldness is associated with a deficiency in oxygen supply to body tissue. The results indicate that penetration of oxygen was lower in the bald frontal scalp than in hair-bearing temporal scalp area. As such, good blood supply to the scalp is essential to maintain normal cycle of hair growth.

Tocotrienol, a form of vitamin E, is a potent anti-oxidant and has been found useful in combating many health problems. While there was a report of the beneficial effects of vitamin E in hair care products (Shipp, 1994), its potential in the restoration of hair in patients taking tocotrienols as a supplement has yet to be explored. Thus, the aim of the present study was to investigate the possible intervention effects on hair loss with tocotrienols.

Vitamin E consists of 8 molecules or isoforms; four of which are known as tocopherols and four of which are known as tocotrienols. Structurally, both consist of a chromanol head and a phytyl side chain. The difference between tocopherols and tocotrienols lies in the phytyl side chain. Whereas the phytyl side chain of tocopherols is fully saturated, that of the tocotrienols has three double bonds at the 3, 7 and 11 positions. Both tocopherols and tocotrienols are further designated as alpha-, beta-, gamma- and delta-isoforms depending on the number and position of the methyl groups on the chromanol ring. Thus, tocopherols and tocotrienols are distinctively different and are not derivatives of each other (Theriault et al, Clinical Biochemistry (1990) 32(5):309).

Because of the difference observed in the phytyl chain of tocopherols and tocotrienols, the two series have also been reported to possess differences in biological activities, with the tocotrienols reportedly to be superior (Qureshi et al, J Biol Chem (1986) 261:10544; Serbinova et al, Free Radic Biol Med (1991) 10:263). Moreover, the half life of tocopherols in humans has been reported to be about 20 hours while the half-life of tocotrienols was reported to be between 2–4 hours only.

Although tocopherols have been mentioned in other patents describing hair growing agents, tocopherols are not the major active ingredient but merely act as formulation aid, as mentioned in some of the patents. The patent by Kamimura (European Patent Application Number EP1232740A2) relates to a hair growing agent, comprising phosphatidic acid as an active ingredient (as claim 1). Only in the subsequent claims did the inventor mention that "A hair-growing agent comprising, as active ingredients, the phosphatidic acid, and one or more members selected from the group consisting of proanthocyanidin, tocopherol, derivatives of tocopherol, panthothenic acid . . . ". Moreover, the above patent only mentioned tocopherol as one of the components of the invention and not tocotrienols per se. It should be emphasized that tocotrienols are distinctly different from tocopherols.

In the patent by Mitsuyama (JP2000038340), it relates to peroral hair growth stimulants containing minoxidil AND one or more compounds chosen from a group of molecules which may consist of vitamin E. The emphasis was on minoxidil and not Vitamin E although Vitamin E as a group encompasses both tocopherol and tocotrienols. Tocotrienols were not being mentioned at all for preventing hair loss as the sole active ingredient but instead vitamin E was used more as a supplement to minoxidil or as an excipient in the preparation. On the other hand, the present invention specifically relates to preparations containing tocotrienols for promoting hair growth and not in combination with other molecules.

U.S. Pat. No. 4,439,432 (Peat) relates to the use of progesterone solubilized in tocopherol for the correction of progesteron deficiency states. The tocopherol in the preparation was not indicated for the treatment of any ailments listed in the patent, which include abnormal hair growth resulting from androgen excess, but rather the tocopherol was used as a non-toxic solvent to solubilize the progesteron such that it did not crystallize out upon mixing with biological fluids. The tocopherol used in the U.S. Pat. No. 4,439,432 was not meant to exert any therapeutic action. Tocopherol in this case was used solely as an inert excipient/carrier for progesterone so that the progesterone would not crystallize out as in the case of a prior art where ethanol was used. U.S. Pat. No. 5,591,772 by Lane et al. relates to the use of novel tocotrienols and tocotrienol-like compounds as hypocholesterolemic, antithrombotic, antioxidizing, anti-atherogenic, anti-inflammatory and immunoregulatory agents. It was never mentioned in the patent that tocotrienols could be used for promoting hair growth or preventing hair loss as stated in the present invention. Hence, the aim of the present study was to investigate the possible intervention effects on hair loss with tocotrienols.

BRIEF SUMMARY OF THE INVENTION

Accordingly, it is the primary objective of the present invention to provide a mixed tocotrienols composition. It is also another objective to provide a formulation for promoting hair growth and preventing hair loss using the mixed tocotrienols of the present invention.

This and other objectives of the present invention are accomplished by: (1) a mixed tocotrienols composition; (2) a formulation for promoting hair growth and preventing hair loss in a mammal wherein mixed tocotrienols are combined with a pharmaceutically acceptable excipient; (3) a formulation for promoting hair growth and preventing hair loss in a mammal wherein α-, or γ-, or δ- tocotrienols is combined with pharmaceutically acceptable excipient; and (4) the use of a formulation as claimed in the present invention for promoting hair growth and preventing hair loss in a mammal.

The formulation according to the present invention, when administered orally or topically, promotes hair growth and prevents hair loss, and the number of hairs appears to increase in those persons experiencing hair loss.

BRIEF DESCRIPTION OF THE DRAWING

Other aspects of the present invention and their advantages will be discerned after studying the Detailed Description in conjunction with the accompanying figure in which are provided for illustrative but not limiting purposes.

DETAILED DESCRIPTION OF THE INVENTION

Figure 1:
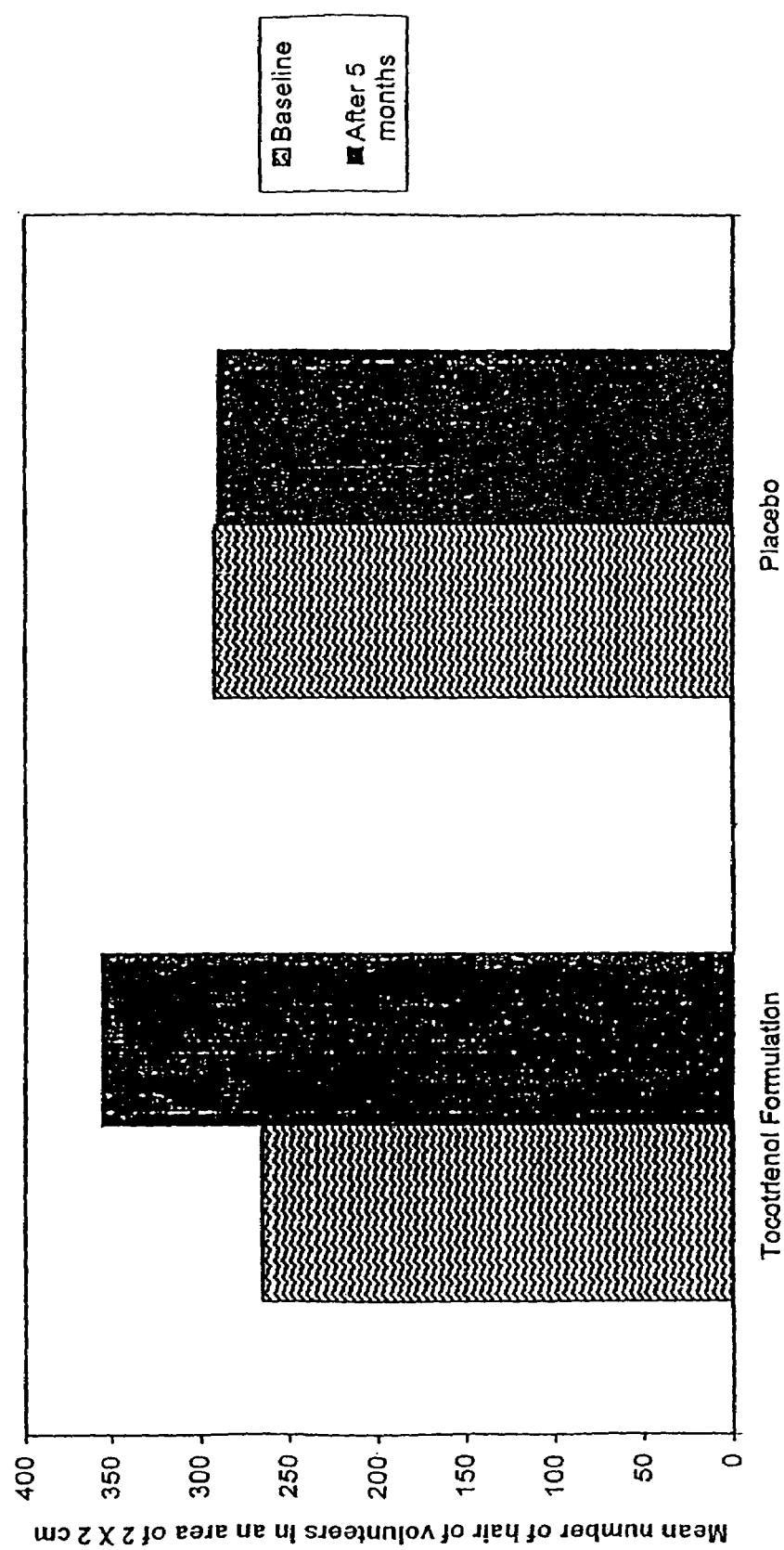
FIG. 1 shows the effect of the tocotrienol formulation according to the present invention on the mean number of hairs of volunteers after supplementation for 5 months.

Effect Of Tocotrienol Supplementation On Hair Growth
Study Design

A randomized, double blind, placebo-controlled two groups parallel study was conducted to compare the effect of a mixture of tocotrienols, comprising α-, γ-, and δ-tocotrienols and alpha-tocopherol, with placebo on hair growth. All volunteers were randomized to receive one capsule comprising either (i) a mixture of tocotrienols and alpha-tocopheral, or (ii) a placebo, twice daily after food over a period of at least 5 months. They were seen for an efficacy evaluation every month throughout the study. The control was a placebo capsule containing 600 mg of soya bean oil, and the tocotrienol formulation consisted of capsules containing a mixture of about 50 mg of tocotrienols and about 23 i.u. alpha-tocopherol. The entire study took 15 months for completion.

Although the preferred embodiment of the formulation is in the form of soft gelatin capsule, other oral pharmaceutical dosage forms are not excluded. The preferred dosage range of tocotrienols for oral consumption is from about 20 mg to about 1500 mg/day. The formulation may also be applied topically and may be in the form of a cream, a lotion, an ointment, a gel, a liquid, or any other topical form. The concentration of tocotrienols used in the topical formulation is about 1.0%, and the minimum concentration of tocotrienols in any formulation is about 0.1%.

Inclusion Criteria

Volunteers of 15 years of age or older and in good general health were recruited into the study. Alopecia must have present for least 2 months and the areas alopecia must not have any visual evidence of new hair growth. Volunteers previously exposed to minoxidil were ineligible to participate in the study, as were patients who have used hair-restorers or systemic drugs like steroids, antihypertensives, cytotoxic compounds, vasodilators, anticonvulsant drugs, β-blockers, spironolactone, cimetidine, ketoconazole, estrogens or progesterons within the previous three months. Patients experiencing hair loss due to thyroid disease, adverse drug reactions, scalp or hair trauma, structural hair shaft abnormalities and lichen planus were excluded from the study.

Efficacy Evaluation

Two parameters were chosen to evaluate the efficacy of tocotrienols and alpha-tocopherol supplementation:

i) Hair count—hair count served as the primary efficacy measure. An area of 2×2 cm was selected in the area of hair thinning for each patient, and the two opposing corners of the square were permanently marked (using a 4 $cm^2$ wire template) to ensure that the hair in the same area was counted at each visit.

ii) Weight of hair—a small tuft of hair (at least 20 strands) within the demarcated area was clipped horizontally. Twenty strands were randomly chosen and cut into 1 cm in length. The total weight was obtained using a microbalance and the mean weight was recorded.

All of the two parameters were obtained at baseline and every month thereafter during the study. Only the terminal hair growth was recorded and analyzed.

Results of Hair Growth Studies

Nineteen patients (14 men and 5 women) entered the study and completed at least the first 5 months of therapy. Their ages ranged from 23 to 59 years. The mean duration of current alopecia episode was approximately 5 years. The extent of alopecia was as follows: less than 25%, 6 patients; 25–49%, 8 patients; 50–74%, 4 patients; 75–99%, 1 patient.

Eleven volunteers were randomized to receive the tocotrienol formulation supplementation while 8 volunteers were in the placebo group. Comparability of the treatment groups with respect to initial hair counts as well as the weight of hair was assessed. No statistically significant difference between treatment groups was detected for any of the above characteristics.

At the end of the supplementation period, all volunteers in the tocotrienol formulation group had positive results, recording an increase in the number of hairs in the evaluation area. Seven volunteers (64%) showed regrowth of between 10–35% while 3 volunteers (27%) had 50% or greater regrowth. One volunteer had regrowth of more than 100%. The mean percentage of increase in the number of hairs is 42.4±40.9% (mean±SD). (Table 1 and FIG. 1). The increase is statistically significant ($p<0.05$) when analyzed using paired sample t-test. On the other hand, of the total eight volunteers in the placebo group, two showed hair regrowth, two had hair loss while the other four did not show any significant changes in the number of hairs. The mean percentage of increase was 1.4±13.8%. No statistically significant difference ($p>0.05$) in the number of hairs was detected between baseline and post-supplementation, thus indicating that the placebo effect did not occur during this study.

However, in terms of the weight of the hair, no statistically significant difference (p>0.05) between pre- and post-supplementation was detected for both groups of volunteers (tocotrienol and placebo). The mean percentage of weight increment was 16.4±42.5% in the tocotrienol formulation group while that of the placebo group had an increase of 5.7±40.1%. (Table 2).

The above-mentioned studies therefore indicate that supplementation with a formulation comprising a mixture of tocotrienol, alpha-tocopherol and pharmaceutically acceptable excipient appears to promote hair growth and increase the number of hair in persons experiencing hair loss. The choice of pharmaceutically acceptable excipients will be obvious to those skilled in the relevant art. Acceptable excipients include any inert, compatible substances added to make the final dosage forms, for the formulations, such as tablets, capsules, or soft gelatin capsules. For example, vegetable oil can be added as an excipient to make up the volume for the encapsulation of soft gelatin capsules. As such, a pharmaceutically acceptable excipient includes any excipients that are approved for use by the relevant authorities and are compatible with tocotrienols.

REFERENCES

Bergfeld W F (1995). Androgenetic alopecia: an autosomal dominant disorder. *Am J Med* 98:95S–98S.

Bertolino A P (1993). Clinical hair loss: diagnosis and treatment. *J Dermatol* 20:604–610.

Chen W. Zouboulis and Cafanos C E (1996). The 5-alpha reductase system and its inhibitors. *Dermatology* 193: 177–184.

DeVillez R L, Jacobs J P, Szpunar C A & Warner M L (1994). Androgenetic alopecia in the female. Treatment with 5% topical minoxidil solution. *Arch Dermatol* 130: 303–307.

Goldman B E, Fisher D M and Ringler S L (1996). Transcutaneous PO2 of the scalp in male pattern baldness: a new piece to puzzle. *Plast Reconstr Surg* 97(6):1109–1116.

Hogan D J and Chamberlain M (2000). Male pattern baldness. *South Med J* 93(7):657–662.

TABLE 1

Individual number of hair at baseline and 5 months after tocotrienol and placebo supplementation

| | Tocotrienol | | | | Placebo | | |
|---|---|---|---|---|---|---|---|
| Volunteer | Baseline | 5 months | % change | Volunteer | Baseline | 5 months | % change |
| 1 | 290 | 477 | 64.5 | 1 | 194 | 244 | 25.8 |
| 2 | 380 | 463 | 21.8 | 2 | 391 | 385 | −1.5 |
| 3 | 496 | 603 | 21.6 | 3 | 358 | 369 | 3.1 |
| 4 | 223 | 370 | 65.9 | 4 | 354 | 296 | −16.4 |
| 5 | 110 | 133 | 20.9 | 5 | 223 | 258 | 15.7 |
| 6 | 266 | 358 | 34.6 | 6 | 286 | 267 | −6.6 |
| 7 | 110 | 274 | 149.1 | 7 | 307 | 275 | −10.4 |
| 8 | 258 | 298 | 15.5 | 8 | 219 | 223 | 1.8 |
| 9 | 314 | 344 | 9.6 | | | | |
| 10 | 287 | 316 | 10.1 | | | | |
| 11 | 179 | 274 | 53.1 | | | | |
| Mean | 264.8 | 355.5 | 42.4 | Mean | 291.5 | 289.6 | 1.4 |
| SD | 112.9 | 124.7 | 40.9 | SD | 73.6 | 58.2 | 13.8 |

TABLE 2

Individual weight of hair (g) at baseline and 5 months after tocotrienol and placebo supplementation.

| | Tocotrienol | | | | Placebo | | |
|---|---|---|---|---|---|---|---|
| Volunteer | Baseline | 5 months | % change | Volunteer | Baseline | 5 months | % change |
| 1 | 0.0920 | 0.1078 | 17.2 | 1 | 0.2280 | 0.1200 | −47.4 |
| 2 | 0.0970 | 0.0962 | −0.8 | 2 | 0.0915 | 0.0945 | 3.3 |
| 3 | 0.2490 | 0.2480 | −0.4 | 3 | 0.1974 | 0.1956 | −0.9 |
| 4 | 0.0732 | 0.1552 | 112.0 | 4 | 0.0822 | 0.1587 | 93.1 |
| 5 | 0.1055 | 0.0849 | −19.5 | 5 | 0.1899 | 0.1789 | −5.8 |
| 6 | 0.1315 | 0.1577 | 19.9 | 6 | 0.1158 | 0.1206 | 4.1 |
| 7 | 0.1094 | 0.1295 | 18.4 | 7 | 0.1398 | 0.1625 | 16.2 |
| 8 | 0.1405 | 0.1686 | 20.0 | 8 | 0.1187 | 0.0988 | −16.8 |
| 9 | 0.1284 | 0.0837 | −34.8 | | | | |
| 10 | 0.1380 | 0.2348 | 70.1 | | | | |
| 11 | 0.1692 | 0.1317 | −22.2 | | | | |
| Mean | 0.1 | 0.1 | 16.4 | Mean | 0.1 | 0.1 | 5.7 |
| SD | 0.0 | 0.1 | 42.5 | SD | 0.1 | 0.0 | 40.1 |

Shipp J J (1994). Hair care products. In: *Chemistry and technology of the cosmetics and toiletries industry*. (Williams DF and Schmitt WH, ed.s), p 66. Blackie Academic & Professional: UK.

Setty L R (1970). Hair pattern of the scalp of white and Negro males. *Am J. Phys Anthropol* 33:40–55.

Trancik R J (1998). Update on topical minoxidil in hair loss. *Annual Meeting of American Academy of Dermatology, Orlando.*

While the preferred embodiment of the present invention has been described, it should be understood that various changes, adaptations and modifications may be made thereto. It should be understood, therefore, that the invention is not limited to details of the illustrated invention shown in the figure and tables, and that variations in such minor details will be apparent to one skilled in the art.

The invention claimed is:

1. A method of promoting hair growth and reducing hair loss in a mammal in need thereof consisting of administering to said mammal a composition consisting of mixed tocotrienols, alpha-tocopherol and a pharmaceutically acceptable excipient, wherein the minimum concentration of said mixed tocotrienols is about 0.1%, and wherein said composition is administered in the form of an oral dosage.

2. The method of claim 1, wherein said mixed tocotrienols are a mixture of $\alpha$-, $\gamma$-, and $\delta$- tocotrienols.

3. The method of claim 1, wherein said oral dosage is in the form of a soft gelatin capsule.

4. The method of claim 1, wherein an oral administration of said composition is at a dosage of about 20 mg–1500 mg per day.

5. A method for promoting hair growth and reducing hair loss consisting of administering to a mammal in need thereof a pharmaceutically acceptable excipient, alpha-tocopherol and a tocotrienol selected from the group consisting of $\alpha$-, $\gamma$-, and $\delta$- tocotrienols, wherein the: minimum concentration of said tocotrienol is about 0.1%, and wherein said pharmaceutically acceptable excipient, said alpha-tocopherol and said tocotrienol are administered in the form of an oral dosage.

6. The method of claim 5, wherein the amount of said tocotrienols is about 50 mg.

7. The method of claim 5, wherein said oral dosage is in the form of a soft gelatin capsule.

8. The method of claim 5, wherein an oral administration of said composition is at a dosage of about 20 mg –1500 mg per day.

* * * * *

UNITED STATES PATENT AND TRADEMARK OFFICE
CERTIFICATE OF CORRECTION

| | | |
|---|---|---|
| PATENT NO. | : 7,211,274 B2 | |
| APPLICATION NO. | : 11/120268 | |
| DATED | : May 1, 2007 | |
| INVENTOR(S) | : David Sue San Ho et al. | |

It is certified that error appears in the above-identified patent and that said Letters Patent is hereby corrected as shown below:

On the title page item [73] a typographical error in the printed name of the Assignee should be corrected. "Hovis SDN BHD" should be changed to --Hovid SDN BHD--.

Signed and Sealed this

Twenty-fifth Day of December, 2007

JON W. DUDAS
*Director of the United States Patent and Trademark Office*